United States Patent
Er

(10) Patent No.: US 6,185,461 B1
(45) Date of Patent: Feb. 6, 2001

(54) SYSTEM AND METHOD FOR VERIFICATION OF RECOMMENDED REPLACEMENT TIME INDICATION IN AN IMPLANTABLE CARDIAC STIMULATION DEVICE

(75) Inventor: Siew Bee Er, Newhall, CA (US)

(73) Assignee: Pacesetter, Inc., Sylmar, CA (US)

(*) Notice: Under 35 U.S.C. 154(b), the term of this patent shall be extended for 0 days.

(21) Appl. No.: 09/108,830

(22) Filed: Jul. 1, 1998

(51) Int. Cl.[7] ............................ A61N 1/378; A61N 1/362
(52) U.S. Cl. ................................................ 607/27; 607/29
(58) Field of Search .......................................... 607/27, 29

(56) References Cited

U.S. PATENT DOCUMENTS

| | | | |
|---|---|---|---|
| 4,448,197 | * | 5/1984 | Nappholz et al. . |
| 4,940,052 | | 7/1990 | Mann et al. . |
| 5,391,193 | * | 2/1995 | Thompson ............................ 607/29 |
| 5,507,786 | * | 4/1996 | Morgan et al. . |
| 5,620,474 | * | 4/1997 | Koopman ............................ 607/29 |
| 5,722,999 | * | 3/1998 | Snell . |
| 5,741,307 | * | 4/1998 | Kroll . |
| 5,749,907 | * | 5/1998 | Mann . |
| 5,800,472 | * | 9/1998 | Mann . |
| 5,868,794 | * | 2/1999 | Barkley et al. . |
| 5,925,068 | * | 7/1999 | Kroll . |
| 6,108,579 | * | 8/2000 | Snell et al. . |

* cited by examiner

Primary Examiner—Carl H. Layno

(57) ABSTRACT

An implantable stimulation device is interrogated by an external programmer, operated by a medical practitioner, to determine whether a recommended replacement time indicator in the device is set to an active state. If the recommended replacement time indicator is active, the programmer displays the active indicator and an accompanying message explaining various causes that may result in the indicator being set to the active state. The programmer then retrieves battery diagnostic data, which may include, but is not limited to battery test rate, battery voltage, battery current, and battery impedance, and optionally generates a battery longevity prediction graph. The battery diagnostic data and the prediction graph are then displayed by the programmer to the medical practitioner. The medical practitioner may then analyze the battery diagnostic data and the prediction graph to determine whether the recommended replacement time indicator was properly set by the implantable stimulation device to the active state. Finally, the medical practitioner can use the programmer to reset an improperly set recommended replacement time indicator to the inactive state.

17 Claims, 2 Drawing Sheets

SYSTEM AND METHOD FOR VERIFICATION OF RECOMMENDED REPLACEMENT TIME INDICATION IN AN IMPLANTABLE CARDIAC STIMULATION DEVICE

FIELD OF THE INVENTION

The present invention relates in general to implantable cardiac stimulation devices, including bradycardia and anti-tachycardia pacemakers, defibrillators, cardioverters and combinations thereof that are capable of measuring physiological data and parametric data pertaining to implantable medical devices. More particularly, this invention relates to a system and method for verifying recommended replacement time indication in an implantable cardiac stimulation device.

BACKGROUND OF THE INVENTION

Implantable medical devices, such as pacemakers, defibrillators and cardioverters (collectively referred to as implantable cardiac stimulating devices) are designed to monitor and stimulate the heart of a patient that suffers from a cardiac arrhythmia. Using leads connected to a patient's heart, these devices typically stimulate the cardiac muscles by delivering electrical pulses in response to measured cardiac events which are indicative of a cardiac arrhythmia. Properly administered therapeutic electrical pulses often successfully reestablish or maintain the heart's regular rhythm.

Implantable cardiac stimulation devices (hereinafter "implantable stimulation devices") can treat a wide range of cardiac arrhythmias by using a series of adjustable parameters to alter the energy, shape, location, and frequency of the therapeutic pulses. The adjustable parameters are usually defined in a computer program stored in a memory of the implantable stimulation device. The program (which is responsible for the operation of the implantable device) can be defined or altered telemetrically by a medical practitioner using an implantable device programmer. Modern implantable stimulation devices have a great number of adjustable parameters that must be tailored to a particular patient's therapeutic needs. In addition, implantable stimulation devices also have a significant number of diagnostic parameters that, when retrieved from an implantable stimulation device by the medical practitioner using the implantable device programmer, inform the medical practitioner about the operational characteristics of the implantable stimulation device and the device components.

One diagnostic parameter of particular importance in an implantable stimulation device is the recommended replacement time of the device. Electrical energy necessary to maintain proper operation of an implantable stimulation device is provided by a battery connected to energy-consuming components of the device such as a pulse generator, the memory, and control circuitry. The battery differs from other implantable stimulation device components in that other device components are typically designed to last indefinitely, while available energy of the battery is consumed during its normal use. Eventually, output voltage of the battery falls to a level that is insufficient to operate the implantable stimulation device within limits specified by the therapeutic requirements of the device. By this time the battery is no longer useful and must therefore be replaced. Because the battery is typically built into the implantable device casing, replacement of the battery requires a surgical procedure to replace the implanted device with a new device equipped with a fully charged battery.

It is highly desirable to predict this failure of the battery well in advance so that arrangements may be made for replacement of the implantable stimulation device in which the battery is at or approaching very low capacity. Thus, the concept of a recommended replacement time for implantable stimulation devices has been developed to provide ample warning to a medical practitioner that a particular device with a battery reaching dangerously low capacity may need to be replaced in the near future.

To implement this concept, most modern implantable stimulation devices incorporate battery diagnostic circuitry that monitors the condition and operational characteristics of the battery. A recommended replacement time indicator, defined as a diagnostic parameter and stored in the device memory, is set by the device to an active state when the battery diagnostic circuitry determines that the battery has reached its recommended replacement time.

After initial implantation and configuration of the implantable stimulation device, the medical practitioner typically performs periodic follow-up examinations to determine whether the therapy delivered by the device is having the desired effect and the device is otherwise operating properly. In particular, it is of utmost importance to determine whether the recommended replacement time indicator has been set to the active state so that the medical practitioner may plan for possible device replacement.

However, the recommended replacement time indicator may be accidentally set to the active state even though the battery has not yet reached its recommended replacement time. This may occur for a number of reasons—for example, the indicator may be set to the active state due to high output pacing by the device, by externally delivered defibrillation, or by defibrillation delivered by an implantable defibrillator. As a result, the active recommended replacement time indicator may erroneously indicate that the implantable stimulation device needs to be replaced—a highly undesirable situation.

It would thus be desirable to provide a system and method for assisting the medical practitioner in verifying whether an active recommended replacement time indicator has been properly set by the implantable stimulation device. It would further be desirable to enable the medical practitioner to change an improperly set recommended replacement time indicator to an inactive state.

SUMMARY OF THE INVENTION

The disadvantages and limitations discussed above are overcome by the present invention. In accordance with the invention, a system and method are provided for assisting a medical practitioner in verifying whether recommended replacement time indication in an implantable cardiac stimulation device (hereinafter implantable stimulation device) is proper. The system and method of the present invention also utilize data acquisition and display capabilities of an implantable device programmer to enable the medical practitioner to verify whether an active recommended replacement time indicator was properly set to active status by the implantable stimulation device. The programmer may also be used to change an improperly set recommended replacement time indicator to an inactive state. All of the aforesaid advantages and features are achieved without incurring any substantial relative disadvantage.

The present invention provides an implantable stimulation device equipped with data acquisition and telemetric communication capabilities, and also provides an implantable device programmer, preferably in the form of a portable computer, with data processing, data storage, graphical data display, data output, data communication, telemetric communication, and diagnostic capabilities.

The implantable stimulation device of the present invention includes a control system for controlling its operation, a set of leads for receiving atrial and/or ventricular signals and for delivering atrial and ventricular stimulation pulses, a set of amplifiers for amplifying the atrial and ventricular signals, and pulse generators for generating atrial and ventricular stimulation pulses. In addition, the implantable stimulation device includes memory for storing diagnostic parameters such as battery diagnostic data for later retrieval by the medical practitioner using an external programmer, and a telemetry circuit for communicating with the external programmer. The implantable stimulation device also includes a battery for providing electrical energy to all of its energy-consuming components.

The programmer of the present invention includes a control system for controlling the operation of the programmer and for analyzing data acquired from the implantable stimulation device, a user input device for enabling the medical practitioner to issue commands to the programmer and to the implantable stimulation device and an output device such as a video display for displaying data and images to the medical practitioner. The programmer also includes a memory for storing data and programs that perform various programmer functions and procedures, and a data acquisition device, such as a telemetry wand, for communicating with the implantable stimulation device. Finally, a remote communication device, such as a modem, may be connected between the telemetry circuit of the implantable stimulation device and the data acquisition device of the programmer to enable remote communication therebetween.

In a preferred embodiment of the present invention, the medical practitioner uses the programmer to interrogate the pacemaker to determine whether a recommended replacement time indicator in the pacemaker is set to an active state. If the recommended replacement time indicator is active, the programmer displays the active indicator and an accompanying message explaining various events and/or circumstances that may have resulted in the active state of the indicator. The medical practitioner is then prompted to indicate whether the system should proceed with verification of the active recommended replacement time indicator. If the medical practitioner indicates that the system should not proceed, the programmer ends execution of the recommended replacement time indicator verification program. If, on the other hand, the medical practitioner indicates that the system should proceed, then the programmer retrieves battery diagnostic data which may include, but is not limited to, battery test rate, battery voltage, battery current, and battery impedance, and optionally generates a battery longevity prediction graph. The battery diagnostic data and the prediction graph are then displayed or output by the programmer to the medical practitioner. The medical practitioner may then analyze the battery diagnostic data and the prediction graph to determine whether the recommended replacement time indicator was properly set by the implantable stimulating device to the active state. Finally, the medical practitioner can use the programmer to set an improperly set recommended replacement time indicator to the inactive state.

The system and method of the present invention thus greatly assist the medical practitioner in verifying whether an active recommended replacement time indicator has been properly set by the implantable stimulating device, and enable correction by the medical practitioner of an improperly set indicator.

BRIEF DESCRIPTION OF THE DRAWINGS

The above and further features, advantages and benefits of the invention will become apparent in the following description taken in conjunction with the following drawings. It is to be understood that the foregoing general description and the following detailed description are exemplary and explanatory but are not to be restrictive of the invention. The accompanying drawings, which are incorporated in and constitute a part of this invention, illustrate one of the embodiments of the invention and, together with the description, serve to explain the principles of the invention in general terms. Like numerals refer to like parts throughout the disclosure.

DETAILED DESCRIPTION OF THE PREFERRED EMBODIMENTS

The system and method of the present invention utilize an implantable stimulating device and an external programmer operable by a medical practitioner to greatly assist the practitioner in verifying whether an active recommended replacement time indicator has been properly set by the implantable stimulating device and to enable the practitioner to correct an improperly set indicator. While the present invention is described by way of illustrative example with reference to a dual chamber pacemaker, it will be understood that the inventive system and method may be implemented in conjunction with any implantable stimulating device, such as a single chamber pacemaker, a cardioverter, or a cardioverter/defibrillator.

Figure 1:
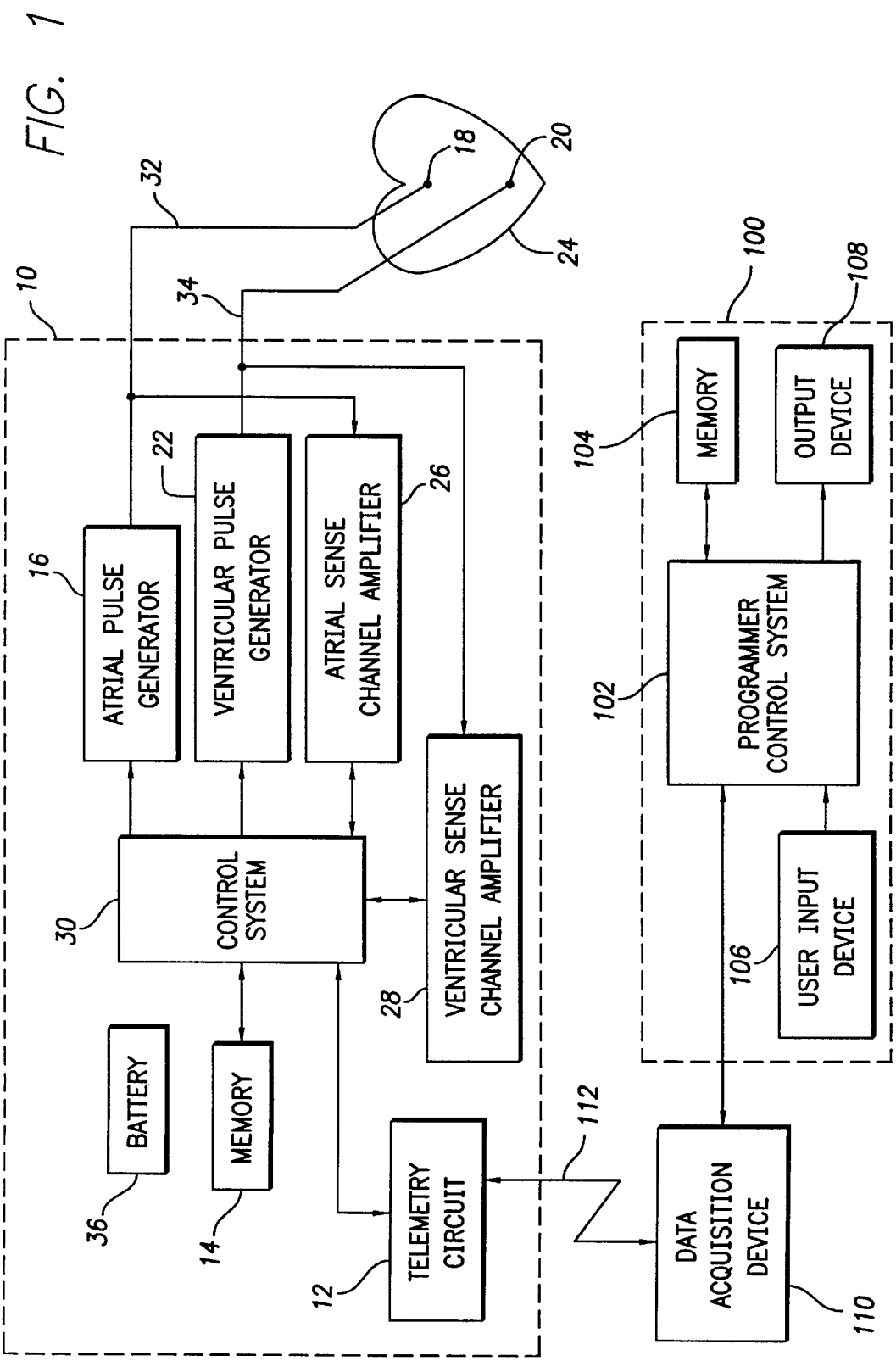
FIG. 1 is a block diagram of a dual chamber pacemaker and a programmer in accordance with the principles of the present invention.

A pacemaker 10 in accordance with this invention is shown in FIG. 1. The pacemaker 10 is coupled to a heart 24 by way of leads 32 and 34, the lead 32 having an electrode 18 which is in contact with one of the atria of the heart 24, and the lead 34 having an electrode 20 which is in contact with one of the ventricles. The lead 32 carries stimulating pulses to the electrode 18 from an atrial pulse generator 16, while the lead 34 carries stimulating pulses to the electrode 20 from a ventricular pulse generator 22. In addition, electrical signals from the atria are carried from the electrode 18, through the lead 32 to the input terminal of an atrial sense amplifier 26. Electrical signals from the ventricles are carried from the electrode 20, through the lead 34 to the input terminal of a ventricular sense amplifier 28.

Controlling the dual chamber pacemaker 10 is a control system 30. The control system 30 is preferably a microprocessor-based system such as that disclosed in commonly-assigned U.S. Pat. No. 4,940,052 of Mann, which is herein incorporated by reference in its entirety. The control system 30 also includes a real-time clock (not shown) for providing timing for monitoring cardiac events and for timing the application of therapeutic pulses by the pulse generators 16 and 24.

The pacemaker 10 also includes a memory 14 which is coupled to the control system 30. The memory 14 allows certain control parameters used by the control system 30 in controlling the operation of the pacemaker 10 to be programmably stored and modified, as required, in order to customize the operation of the pacemaker 10 to suit the needs of a particular patient. In addition, diagnostic parameters representative of operational characteristics of the components of the pacemaker 10, such as a recommended replacement time indicator for a battery 36, are stored in the memory 14 for later retrieval and analysis.

The control system 30 receives the output signals from the atrial amplifier 26. Similarly, the control system 30 also receives the output signals from the ventricular amplifier 28. These output signals are generated each time that an atrial event or a ventricular event is sensed within the heart 24.

The control system 30 also generates an atrial trigger signal which is sent to the atrial pulse generator 16, and a ventricular trigger signal which is sent to the ventricular pulse generator 22. These trigger signals are generated each time that a stimulation pulse is to be generated by one of the pulse generators 16 or 22.

A telemetry circuit 12 is further included in the pacemaker 10 and connected to the control system 30. The telemetry circuit 12 may be selectively coupled to an external programmer 100 by means of an appropriate communication link 112. The communication link 112 may be an electromagnetic telemetry link or a remote communication link such as a pair of modems interconnected via a telecommunications link and equipped with telemetry capabilities.

The pacemaker 10 also includes the battery 36 connected to the various energy-consuming components of the pacemaker 10 (e.g. the control system 30 and the pulse generators 16 and 22). The battery may be of any type commonly used in implantable stimulating devices such as lithium or lithium iodine. The recommended replacement time indicator is typically in an "inactive" state; however, when the control system 30 determines that the battery 36 has reached its recommended replacement time, the control system 30 sets the recommended replacement time indicator to an "active" state. Various advantageous approaches to determining whether the battery 36 has reached its recommended replacement time are well known in the art, and any such approach may be utilized in accordance with the invention as a matter of design choice. When the medical practitioner uses the programmer 100 to interrogate the pacemaker 10, the medical practitioner is alerted, by the active status of the recommended replacement time indicator, that the pacemaker 10 may need to be explanted and replaced.

Undesirably, the recommended replacement time indicator may be accidentally set to the active state even though the battery 36 has not yet reached its recommended replacement time. This may occur for a number of reasons—for example, the indicator may be set to the active state due to high output pacing by the pulse generators 16 and/or 22, by externally delivered defibrillation or by defibrillation delivered by an implantable defibrillator. It is the purpose of the present invention to assist the medical practitioner in verifying whether an active recommended replacement time indicator has been properly set by the control system 30.

The programmer 100 is controlled by a programmer control system 102, which is preferably microprocessor-based. A programmer memory 104 is used by the programmer control system 102 for software operation, data processing, and long-term data storage. The programmer memory 104 may include random access memory and any type of memory suitable for long-term data storage including a hard disk drive, flash memory, or a rewritable optical disk. Optionally, one or more battery longevity prediction graphing programs may be stored in the programmer memory 102 for selective use by the medical practitioner.

The programmer 100 is also provided with an output device 108. The output device 108 is used to display the status of the recommended replacement time indicator as well as battery diagnostic data obtained from the pacemaker 10. The output device 108 may also display a battery longevity prediction graph generated by the programmer 100. An external data acquisition device 110 is used to communicate with the pacemaker 10 via the communication link 112. The data acquisition device 110 may be a telemetry wand or another type of communication device for wireless communication with the pacemaker 10. The medical practitioner interacts with the programmer 100 through a user input device 106, which may for example be a keyboard, a pen, or a voice interface. Through the user input device 106, the medical practitioner may also issue commands to the pacemaker 10 when the pacemaker 10 is in communication with the programmer 100.

The operation of the pacemaker 10 is generally controlled by a control program stored in the memory 14 and executed by the control system 30. This control program usually consists of multiple integrated program modules, with each module bearing responsibility for controlling one or more functions of the pacemaker 10. For example, one program module may control the delivery of stimulating pulses to the heart 24, while another module may control the determination of the appropriate state of the recommended replacement time indicator. In effect, each program module is a control program dedicated to a specific function or a set of functions of the pacemaker 10.

Similarly, the operation of the programmer 100 is generally controlled by a main control program stored in the programmer memory 104 and executed by the programmer control system 102. This main control program also consists of multiple integrated program modules that correspond to various features of the programmer 100. The control program module dedicated to controlling the procedure for assisting the medical practitioner in verifying whether an active recommended replacement time indicator has been properly set by the pacemaker 10 is described below in connection with FIG. 2. The control program module of FIG. 2 automatically interacts with other appropriate control program modules of the pacemaker 10 to conduct one or more portions of the procedure.

Figure 2:
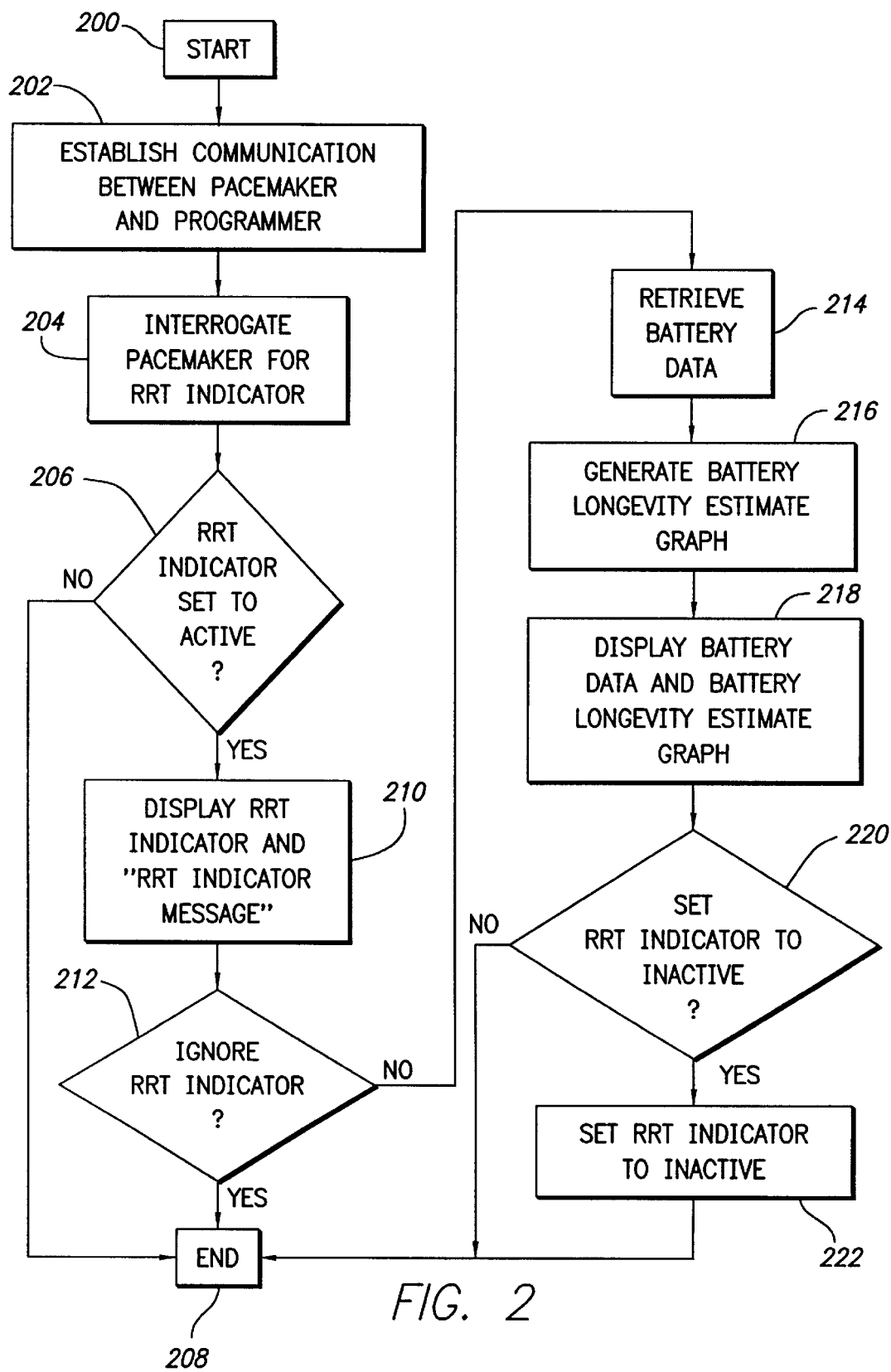
FIG. 2 is a logic flow diagram representing a recommended replacement time indicator verification control program executed by the programmer control system of the programmer of FIG. 1 in accordance with the principles of the present invention.

Shown in FIG. 2 is a logic flow diagram representing the control program module for controlling the procedure for assisting the medical practitioner in verifying whether an active recommended replacement time indicator has been properly set in the pacemaker 10 as executed by the programmer control system 102 of FIG. 1 in accordance with the present invention.

After the control program begins at a step 200, the programmer control system 102 establishes communication between the pacemaker 10 and the programmer 100 at a step 202. At a step 204, the programmer control system 102 retrieves the recommended replacement time indicator from the memory 14, and at a test 206 determines whether the recommended replacement time indicator is set to the active state. If the recommended replacement time indicator is not set to the active state, then the programmer control system 102 proceeds to a step 208 where the execution of the control program module ends. If, on the other hand, the recommended replacement time indicator is determined to be set to the active state, then the programmer control system 102 proceeds to a step 210 where it displays the active recommended replacement time indicator to the medical practitioner. Optionally, at the step 210, the programmer control system 102 also displays a recommended replacement time indicator message to the medical practitioner. Preferably, the recommended replacement time indicator message is composed so as to inform the medical practitioner of various events and/or circumstances that may have caused the pacemaker 10 to properly or improperly set the recommended replacement time indicator to the active state. Examples of such events and circumstances include, but are not limited to, that the battery is substantially at the recommended replacement time, and the occurrence of high output pacing, externally applied defibrillation, or defibrillation by an implantable stimulating device.

At an optional test 212, the medical practitioner is prompted by the programmer control system 102 to indicate whether the recommended replacement time indicator should be ignored. For example, if the medical practitioner is pressed for time and the pacemaker 10 has been recently implanted, the medical practitioner may safely assume that the recommended replacement time indicator has been improperly set. If the medical practitioner chooses to ignore the recommended replacement time indicator, then the programmer control system 102 proceeds to the step 208 where the execution of control program module ends. If, on the other hand, the medical practitioner chooses not to ignore the recommended replacement time indicator, then the programmer control system 102 proceeds to a step 214 at which the system 102 retrieves BATTERY DATA from the memory 14 of the pacemaker 10. BATTERY DATA is preferably a set of diagnostic parameters representative of the characteristics of the battery 36 and that is generated by a self-diagnostic program module executed by the control system 30. BATTERY DATA may include, but is not limited to, battery test rate, battery voltage, battery current, and battery impedance. At an optional step 216, the programmer control system 102 generates a battery longevity prediction graph based on the retrieved BATTERY DATA and other data that may be acquired by or that is stored in the programmer 100. An advantageous technique for generating the battery longevity prediction graph is disclosed in commonly-assigned copending U.S. patent application Ser. No. 08/832,717, filed Apr. 11, 1997, entitled BATTERY MONITORING APPARATUS AND METHOD FOR PROGRAMMERS OF CARDIAC STIMULATING DEVICES, which is incorporated herein by reference in its entirety.

At a step 218, the programmer control system 102 displays the BATTERY DATA, and optionally the battery longevity prediction graph, to the medical practitioner to permit the medical practitioner to review the various characteristics of the battery 36 and determine whether the recommended replacement time indicator has been properly or improperly set to the active state. At a test 220, the programmer control system 102 prompts the medical practitioner to indicate whether the recommended replacement time indicator should be reset to the inactive state. The medical practitioner will most likely wish to reset the recommended replacement time indicator to the inactive state if the practitioner's review of information displayed at the step 218 indicates that the recommended replacement time indicator was improperly set. If the medical practitioner determines that the recommended replacement time indicator was properly set to the active state, the practitioner will most likely keep the recommended replacement time indicator in the active state. In that case, the programmer control system 102 proceeds to the step 208 where execution of the control program module ends. If, on the other hand, the medical practitioner's review of the information displayed at the step 208 indicates that the recommended replacement time indicator was improperly set to the active state, the practitioner will decide at the test 220 to reset the indicator to the inactive state, in which case the programmer control system 102 proceeds to a step 222, where the programmer control system 102 sets the recommended replacement time indicator to the inactive state and then proceeds to the step 208 where execution of the control program module ends.

The medical practitioner is thus assisted in verifying whether an active recommended replacement time indicator has been properly set by the pacemaker 10.

One skilled in the art will appreciate that the present invention can be practiced by other than the described embodiments, which are presented for purposes of illustration and not of limitation, and the present invention is limited only by the claims that follow.

What is claimed is:

1. A system for enabling a medical practitioner to verify whether an implantable stimulation device having a battery for providing electrical energy for operating the implantable stimulating device has reached a recommended replacement time, the system being configured for use with the implantable stimulation device implanted in a patient and a programmer operated by the medical practitioner and configured to communicate with the implantable stimulation device, the system comprising:

first retrieving means in the programmer for retrieving from the implantable stimulating device a recommended replacement time indicator, the indicator being settable by the implantable stimulating device in one of an active state when the implantable stimulation device has substantially reached the recommended replacement time, and an inactive state when the implantable stimulation device has not reached the recommended replacement time;

control means in the programmer for determining whether the recommended replacement time indicator is in the active state;

second retrieving means in the programmer for retrieving from the implantable stimulation device, when the recommended replacement time indicator is determined to be in the active state, battery diagnostic data representative of characteristics of the implantable stimulation device battery;

first display means in the programmer for displaying to the medical practitioner, when the recommended replacement time indicator is determined to be in the active state, the retrieved battery diagnostic data to permit the medical practitioner to verify whether the recommended replacement time indicator has been properly set in the active state;

second display means in the programmer for displaying to the medical practitioner, when the recommended replacement time indicator is determined to be in the active state and prior to activation of said first display means, the active recommended replacement time indicator; and first selection means in the programmer operable for selectively triggering said first display means after said second display means displays the active recommended replacement time indicator.

2. The system of claim 1, further comprising graph generation means connected to said control means and said display means in the programmer for generating a battery longevity prediction graph indicative of predicted longevity of the battery of the implantable stimulation device, wherein said battery diagnostic data includes the battery longevity prediction graph.

3. The system of claim 1, wherein the battery diagnostic data further comprises at least one of battery test rate, battery voltage, battery current, and battery impedance.

4. The system of claim 1, further comprising second selection means in the programmer for selectively setting the recommended replacement time indicator in the implantable stimulation device, when the recommended replacement time indicator is determined to be in the active state and after activation of said first display means, to the inactive state to thereby permit the medical practitioner to reset the recommended replacement time indicator to the inactive state when the recommended replacement time indicator has been improperly set to the active state.

5. The system of claim 1, further comprising third display means in the programmer for displaying to the medical practitioner, when the recommended replacement time indicator is determined to be in the active state and prior to activation of said first display means, a recommended replacement time indicator explanation message representative of a plurality of possible causes for proper activation and for improper activation of the recommended replacement time indicator by the implantable stimulation device to assist the medical practitioner in analyzing the battery diagnostic data.

6. The system of claim 4, wherein the plurality of possible causes for proper and improper activation of the recommended replacement time indicator comprises at least one of the battery is substantially at the recommended replacement time, the battery is near the recommended replacement time, the recommended replacement time indicator has been set to the active state due to high output pacing, the recommended replacement time indicator was set to the active state due to externally applied defibrillation, and the recommended replacement time indicator was set to the active state due to defibrillation by the implantable stimulating device.

7. A system for enabling a medical practitioner to verify whether an implantable stimulation device having a battery for providing electrical energy for operating the implantable stimulating device has reached a recommended replacement time, the system being configured for use with the implantable stimulation device implanted in a patient and a programmer operated by the medical practitioner and configured to communicate with the implantable stimulation device, the system comprising:

a controller in the programmer that:
(i) retrieves a recommended replacement time indicator from the implantable stimulation device, the indicator being settable by the implantable stimulating device in one of an active state when the implantable stimulation device has substantially reached the recommended replacement time, and an inactive state when the implantable stimulation device has not reached the recommended replacement time,
(ii) determines whether the recommended replacement time indicator is in the active state, and
(iii) retrieves from the implantable stimulation device, when the recommended replacement time indicator is determined to be in the active state, battery diagnostic data representative of characteristics of the implantable stimulation device battery; and a display connected to the controller in the programmer, that displays to the medical practitioner, when the recommended replacement time indicator is determined to be in the active state, the retrieved battery diagnostic data to permit the medical practitioner to verify whether the recommended replacement time indicator has been properly set in the active state, wherein said display displays to the medical practitioner, when the recommended replacement time indicator is determined to be in the active state and prior to display of the battery diagnostic data, the active recommended replacement time indicator, and wherein the system further comprises:

selection circuitry connected to the display in the programmer operable to selectively cause said display to display the battery diagnostic data after said display displays the active recommended replacement time indicator.

8. The system of claim 7, further comprising a graph generator connected to said controller and said display in the programmer that generates a battery longevity prediction graph indicative of predicted longevity of the battery of the implantable stimulation device, wherein said battery diagnostic data includes the battery longevity prediction graph.

9. The system of claim 7, wherein the battery diagnostic data further comprises at least one of battery test rate, battery voltage, battery current, battery impedance, and a battery longevity prediction graph.

10. The system of claim 7, further comprising additional selection circuitry connected to the controller in the programmer, operable to selectively set the recommended replacement time indicator in the implantable stimulating device, when the recommended replacement time indicator is determined to be in the active state and after display of the battery diagnostic data by said display, to the inactive state to thereby permit the medical practitioner to reset the recommended replacement time indicator to the inactive state when the recommended replacement time indicator has been improperly set to the active state.

11. The system of claim 7, wherein said display displays to the medical practitioner, when the recommended replacement time indicator is determined to be in the active state and prior to display of the battery diagnostic data, a recommended replacement time indicator explanation message representative of a plurality of possible causes for proper activation and for improper activation of the recommended replacement time indicator by the implantable stimulation device to assist the medical practitioner in analyzing the battery diagnostic data.

12. The system of claim 11, wherein the plurality of possible causes for proper and improper activation of the recommended replacement time indicator comprises at least one of the battery is substantially at the recommended replacement time, the battery is near the recommended replacement time, the recommended replacement time indicator has been set to the active state due to high output pacing, the recommended replacement time indicator was set to the active state due to externally applied defibrillation, and the recommended replacement time indicator was set to the active state due to defibrillation by the implantable stimulating device.

13. A method for enabling a medical practitioner to verify whether an implantable stimulation device implanted in a patient and having a battery for providing electrical energy for operation of the implantable stimulating device, has reached a recommended replacement time, the method being implemented in a programmer operable by the medical practitioner and configured to communicate with the implantable stimulation device, the method comprising the steps of:

(a) retrieving by the programmer from the implantable stimulating device a recommended replacement time indicator, the indicator being settable by the implantable stimulating device in one of an active state when the implantable stimulation device has substantially reached the recommended replacement time, and an inactive state when the implantable stimulation device has not reached the recommended replacement time;

(b) determining by the programmer whether the recommended replacement time indicator is in the active state;

(c) retrieving by the programmer from the implantable stimulation device, when the recommended replacement time indicator is determined to be in the active state, battery diagnostic data representative of characteristics of the implantable stimulation device battery;

(d) displaying by the programmer to the medical practitioner, when the recommended replacement time indicator is determined to be in the active state, the battery diagnostic data to permit the medical practitioner to verify whether the recommended replacement time indicator has been properly set in the active state;

(e) generating, prior to said step (d) by the programmer, a battery longevity prediction graph indicative of predicted longevity of the battery of the implantable stimulation device, wherein said battery diagnostic data includes the battery longevity prediction graph;

(f) displaying by the programmer to the medical practitioner, when the recommended replacement time indicator is determined to be in the active state and prior to said step (d), the active recommended replacement time indicator; and (g) selectively performing said step (d) after performing said step (f).

14. The method of claim 13, further comprising the step of:

(e) generating, prior to said step (d) by the programmer, a battery longevity prediction graph indicative of predicted longevity of the battery of the implantable stimulation device, wherein said battery diagnostic data includes the battery longevity prediction graph.

15. The method of claim 13, further comprising the step of:

(h) displaying by the programmer to the medical practitioner, when the recommended replacement time indicator is determined to be in the active state and prior to said step (d), a recommended replacement time indicator explanation message representative of a plurality of possible causes for proper activation and for improper activation of the recommended replacement time indicator by the implantable stimulation device to assist the medical practitioner in analyzing the battery diagnostic data.

16. The method of claim 13, further comprising the step of:

(i) selectively setting the recommended replacement time indicator in the implantable stimulation device by the programmer under direction of the medical practitioner, when the recommended replacement time indicator is determined to be in the active state and after said step (d), to the inactive state to thereby permit the medical practitioner to reset the recommended replacement time indicator to the inactive state when the recommended replacement time indicator has been improperly set to the active state.

17. The method of claim 13 further comprising the step of:

displaying by the programmer to the medical practitioner, at least one of battery test rate, battery voltage, battery current, battery impedance, and a battery longevity prediction graph.

* * * * *